US00PP23306P2

(12) United States Plant Patent
Barnes

(10) Patent No.: US PP23,306 P2
(45) Date of Patent: Jan. 1, 2013

(54) ***DIEFFENBACHIA* PLANT NAMED 'DELILAH'**

(50) Latin Name: ***Dieffenbachia* hybrid**
Varietal Denomination: Delilah

(76) Inventor: J. Glenn Barnes, Tavares, FL (US)

( * ) Notice: Subject to any disclaimer, the term of this patent is extended or adjusted under 35 U.S.C. 154(b) by 0 days.

(21) Appl. No.: 13/374,133

(22) Filed: Dec. 13, 2011

(51) Int. Cl.
*A01H 5/00* (2006.01)

(52) U.S. Cl. ..... Plt./378

(58) Field of Classification Search ..... Plt./378
See application file for complete search history.

*Primary Examiner* — June Hwu
*Assistant Examiner* — Louanne Krawczewicz Myers
(74) *Attorney, Agent, or Firm* — Penny J. Aguirre

(57) ABSTRACT

A new cultivar of *Dieffenbachia* plant named 'Delilah', that is characterized by its foliage that is variegated with bright creamy white centers, dark green margins, and variable marbling of dark and bright green in the centers, its wide, compact leaf petioles that are variegated with mottling of green and white, its ability to readily produce new shoots resulting in a full and compact plant habit and its thick leaves that impart resistance to insects and diseases.

2 Drawing Sheets

Botanical classification: *Dieffenbachia* hybrid.
Cultivar designation: 'Delilah'.

BACKGROUND OF THE INVENTION

The present invention, *Dieffenbachia* 'Delilah', relates to a new and distinct cultivar of *Dieffenbachia* of hybrid origin, hereinafter referred to as 'Delilah'.

The Inventor discovered the new cultivar, 'Delilah', in his nursery in Apopka, Fla. in January 2007 as a mutation those arose from in vitro propagation of 'Octopus' (not patented).

Asexual reproduction of the new cultivar was first accomplished by stem cuttings by the Inventor in Apopka, Fla. in May 2007. Asexual reproduction of the new cultivar by stem cuttings and tissue culture has shown that the unique features of 'Delilah' are stable and reproduced true to type in successive generations.

SUMMARY OF THE INVENTION

The following traits have been repeatedly observed and represent the characteristics of the new cultivar. These attributes in combination distinguish 'Delilah' as a new and unique cultivar of *Dieffenbachia*.

1. 'Delilah' exhibits foliage that is variegated with bright creamy white centers, dark green margins, and variable marbling of dark and bright green in the centers.
2. 'Delilah' exhibits wide, compact leaf petioles that are variegated with mottling of green and white.
3. 'Delilah' readily produces new shoots resulting in a full and compact plant habit.
4. 'Delilah' exhibits thick leaves that impart resistance to insects and diseases.

The parent plant, 'Octopus', differs from 'Delilah' in having a less compact and full plant habit, in having foliage with centers that are less white in color, and in being less stable during propagation. 'Delilah' can be most closely compared to the cultivars 'Tropic Snow' (not patented) and 'Tropic Marianne' (U.S. Plant Pat. No. 8,832). 'Tropic Snow' is similar to 'Delilah' in having think leaves and foliage with white center s and green margins. 'Tropic Snow' differs from 'Delilah' in being taller in height and producing less shoots therefore having a less compact plant habit, in having more brittle leaves, and in being less accepting of propagation by tissue culture. 'Tropic Marianne' is similar to 'Delilah' in shoot production, leaf shape, and growth habit. 'Tropic Marianne' differs from 'Delilah' in having foliage with leaf centers that are yellow-green in color, in having thinner leaves, and in being less prolific when propagated by tissue culture.

BRIEF DESCRIPTION OF THE DRAWING

The accompanying colored photographs illustrate the overall appearance and distinct characteristics of the new *Dieffenbachia*, 'Delilah'. The photographs were taken of a 1 year-old plant of 'Delilah' as grown as in a greenhouse from a tissue culture plug in Apopka, Fla.

Figure 1:
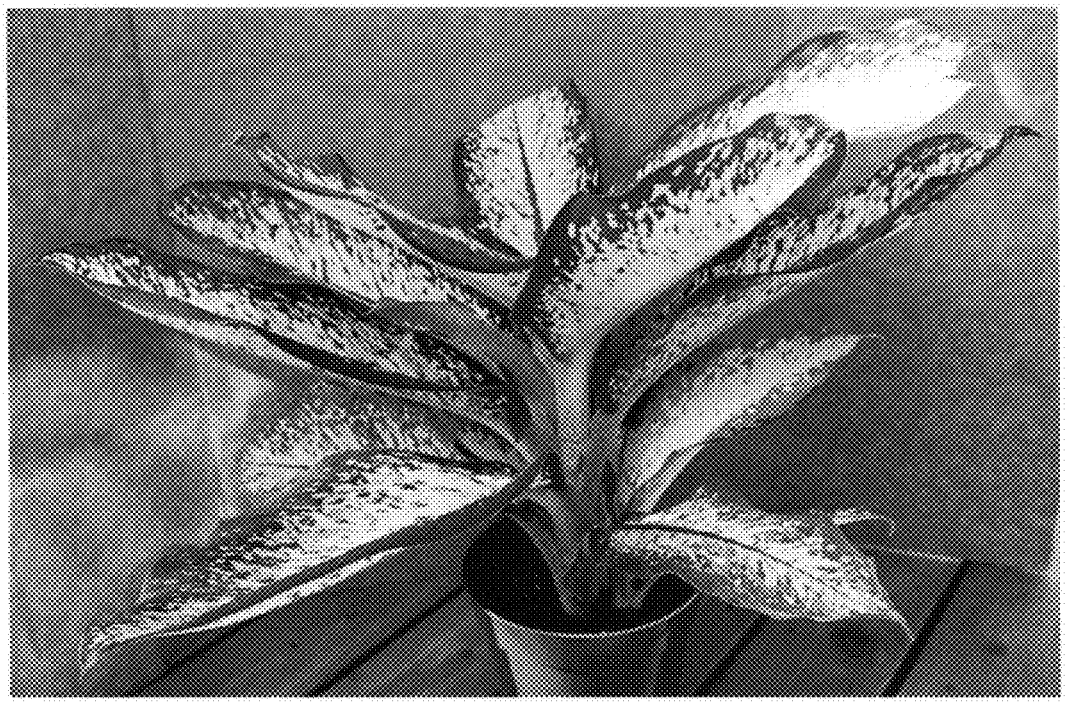
FIG. 1 provides an overall view of the foliage and plant habit of the new cultivar.
Figure 2:
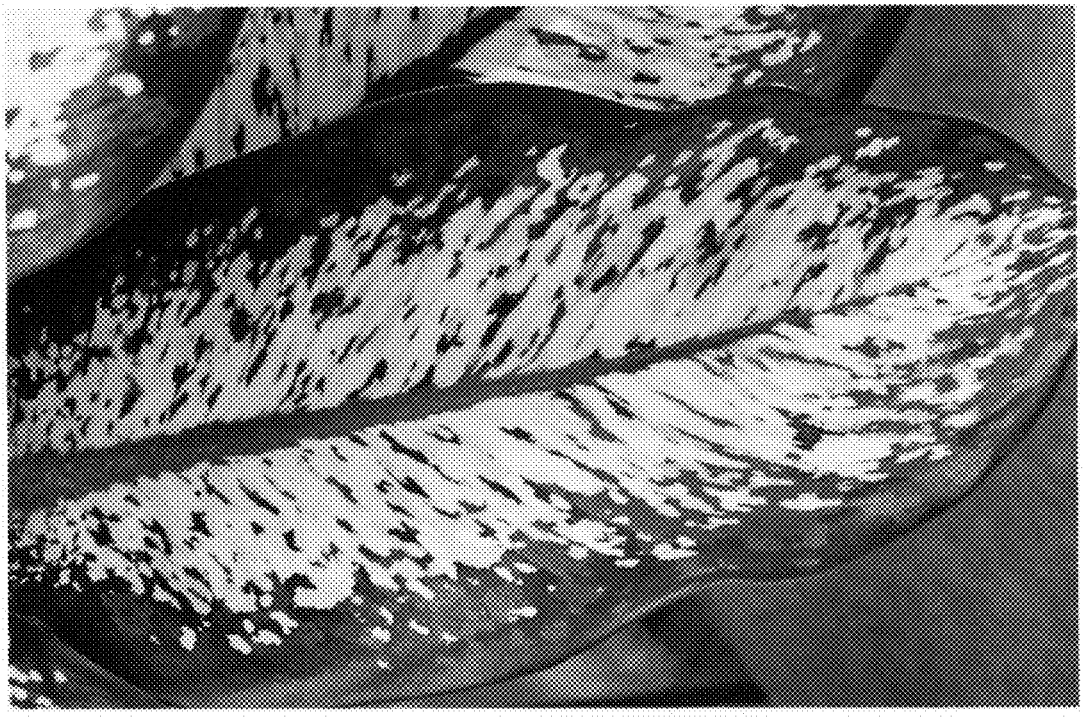

The photograph in FIG. 2 provides a close-up view of a mature leaf of 'Delilah'.

Figure 3:
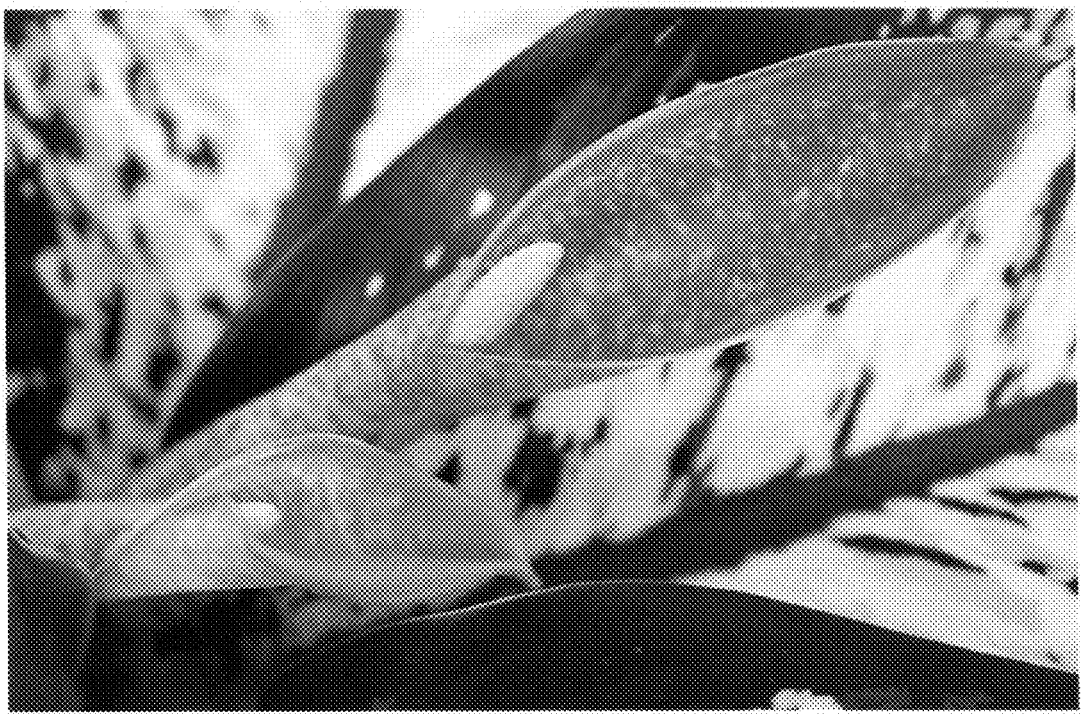

The photograph in FIG. 3 provides a close-up view of an inflorescence of 'Delilah'. The colors in the photographs are as close as possible with the photographic and printing technology utilized and the color values cited in the Detailed Botanical Description accurately describe the colors of the new *Dieffenbachia*.

DETAILED BOTANICAL DESCRIPTION OF THE PLANT

The following is a detailed description of one year-old plants of the new cultivar as grown outdoors in a greenhouse in Apopka, Fla. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—April to August in Florida.

*Plant type*.—Evergreen perennial herb.

*Plant habit*.—Upright, tufted leaves on stout stems.

*Height and spread*.—Reaches about 30 cm in height and 60 cm in width.

*Hardiness*.—Tropical, U.S.D.A. Zones 10b to 11.

*Diseases and pests*.—Thick leaves impart an increased resistance to diseases and pests.

*Root description*.—Fleshy with fibrous secondary roots.

*Propagation*.—In vitro propagation is preferred.

*Growth rate*.—Moderate with a high degree of shoot production.

Stem description:

*Stem size*.—About 24 cm in length and an average of 2.5 cm in width.

*Stem type*.—Stout, surrounded by sheathed leaf petioles.

*Stem color*.—Defined by outer petiole color.

Foliage description:

*Leaf shape*.—Elliptic to broadly lanceolate.

*Leaf division*.—Simple.

*Leaf base*.—Cuneate to auriculate.

*Leaf apex*.—Apiculate.

*Leaf venation*.—Pinnate, mature leaves; mid rib on upper surface is prominent and N137A in color, mid rib on lower surface is conspicuous and closest to 138C in color, color of other veins match leaf coloration.

*Leaf margins*.—Entire, slightly wavy.

*Leaf attachment*.—Petiolate.

*Leaf arrangement*.—Alternate.

*Leaf surface*.—Glabrous on upper surface and lower surface with lower surface slightly waxy.

*Leaf substance*.—Thick, not brittle.

*Leaf orientation*.—Held at about a 45°.

*Leaf aspect*.—Slightly concave upward from mid rib.

*Variegation pattern*.—White centers with mottling of bright and dark green that is more pronounced near margins, dark green margins, mid rib is light green on lower surface and dark green on upper surface, centers become more heavily mottled as the leaves mature.

*Leaf color*.—Emerging foliage, upper surface; mid rib 143C, centers 155C with mottling of 143C and 137A with most of mottling towards margin, margin 137A, emerging foliage lower surface; mid rib 138D, center 155C with mottling of 143C, 144A, and 137C, margin 137C, mature foliage upper surface; mid rib N137A, centers 155C with mottling of 144C and 137A and 137C with more mottling towards margin but increased mottling in center than emerging leaves, margin 137A, mature foliage lower surface; mid rib 138C, centers 155C with mottling of 144A, 137B and 138C, with more mottling towards margin but increased mottling in center than emerging leaves, margin 137B.

*Leaf size*.—Average of 32 cm in length and 17.5 cm in width.

*Leaf quantity*.—About 14 per shoot.

*Petioles*.—About 9 cm in length, an average of 35 mm in width, glabrous surface, sulcate and winged with wing portions about 1.5 cm in width, color upper and lower surface; 155C and heavily mottled with 137A, 137B and 137C.

Flower description:

*Inflorescence type*.—Spathe surrounding a spadix.

*Lastingness of inflorescence*.—About 2 weeks.

*Inflorescence size*.—About 16 cm in length and 2 cm in width.

*Spathe*.—Single bract curled around spadix, about 16 cm in length and 2 cm in width when curled, color of inner and outer surface 157A and mottled with 144A, 144B, 145B and 145C on the bottom curled portion and 137B and with some mottling of 144A and 145C on the top uncurled portion, glabrous on upper and lower surface.

*Inflorescence no*.—An average of 3 per plant.

*Spadix*.—Oblong in shape, an average of 11 cm in length and 8 mm in width, 158A in color, glabrous surface, lower 2.3 is flattened and adnate to spathe (contains perfect flowers) with upper ⅓ round, free, and slightly protruding from spathe opening (contains male flowers and terminal sterile flowers).

*Peduncle*.—About 3 cm in length and 1.2 cm in width, color is a mottling of 145B and 14C, surface is glabrous.

*Petals and sepals*.—None, comprised of reproductive organs only.

*Flower fragrance*.—Slightly pungent.

*Flower no*.—Male: an average of 10, perfect: an average of 20.

*Flower type*.—Male: comprised of 1 to 4 anthers compressed together, no perianth or sepals, perfect: comprised of compound stigma on surface of ovaries and an average of 3 stamens with filaments.

Reproductive organs:

*Gynoecium*.—Compound stigma, about 2.5 mm in diameter and <1 mm in depth, 165A in color with sticky surface, no styles, ovary is about 2.5 cm in diameter, 1.5 cm in depth, and 144A in color.

*Androecium*.—Male flowers; 1 to 3 anthers adhered to spadix, about 1 mm in length and width, 158A in color, no filament visible, pollen was not developed on the plants observed.

*Fruit/seed*.—Seed and berries were not observed.

It is claimed:

1. A new and distinct cultivar of *Dieffenbachia* plant named 'Delilah' as herein illustrated and described.

* * * * *